United States Patent [19]
DeBonte et al.

[11] Patent Number: 5,850,026
[45] Date of Patent: Dec. 15, 1998

[54] CANOLA OIL HAVING INCREASED OLEIC ACID AND DECREASED LINOLENIC ACID CONTENT

[75] Inventors: Lorin R. DeBonte, Fort Collins, Colo.; William D. Hitz, Wilmington, Del.

[73] Assignee: Cargill, Incorporated, Wayzata, Minn.

[21] Appl. No.: 675,650

[22] Filed: Jul. 3, 1996

[51] Int. Cl.$^6$ .............................. A01H 5/00; C12N 5/14; C12N 15/29; C12N 15/52

[52] U.S. Cl. ...................... 800/281; 800/278; 800/286; 800/306; 435/468; 508/101

[58] Field of Search .................................. 800/205, 250, 800/255, DIG. 15, 278, 281, 286, 306; 435/172.3, 468; 508/101

[56] References Cited

U.S. PATENT DOCUMENTS

| | | | |
|---|---|---|---|
| 4,948,811 | 8/1990 | Spinner et al. | 514/560 |
| 5,188,958 | 2/1993 | Moloney et al. | 435/172.3 |
| 5,204,253 | 4/1993 | Sanford et al. | 435/172.3 |
| 5,420,034 | 5/1995 | Kridl et al. | 435/419 |
| 5,428,147 | 6/1995 | Barker et al. | 536/24.1 |

FOREIGN PATENT DOCUMENTS

| | | |
|---|---|---|
| 0 323 753 | 12/1988 | European Pat. Off. |
| 0 647 406 A | 10/1994 | European Pat. Off. |
| WO 92/03919 | 3/1992 | WIPO |
| WO 93/06714 | 4/1993 | WIPO |
| WO 93/11245 | 6/1993 | WIPO |
| WO 93/20216 | 10/1993 | WIPO |
| WO 94/11516 | 5/1994 | WIPO |
| WO 94/24849 | 11/1994 | WIPO |

OTHER PUBLICATIONS

Arondel et al., Science, 258:1353–1355 (1992).
Bailey's Industrial Oil and Fat Products, vol. 2, 4th Ed., John Wiley and Sons, New York (1982).
Downey et al., Can. J. Plant Sci., 43:271–275 (1963).
Eskin et al., JAOCS, 66:1081–1084 (1989).
Garg et al., New England J. Med., 319:829–834 (1988).
Scott Grundy, New England J. Med., 314:745–748 (1986).
Hoffman et al., Theor. Appl. Genet., 61:225–232 (1982).
Jonsson et al., Research amd Results in Plant Breeding, Svalof 1886–1986, pp. 173–184.
Okuley et al., Plant Cell, 6:147–158 (1994).
Pleines et al., Abstract of the Proceedings of the 7th International Rapeseed Congress, Poznan, Poland, May 11–14, 1987.
Pleines et al., Abstract of 43rd Lecture Meeting of Deutsche Gesellschaft fur Gesellschaft fur Fettwissenschaft in Hamburg, Sep. 30–Oct. 11, 1987.
Pleines et al., Fat Sci. Technol., 90(5), 167–171 (1988).
Rakow et al., J. Am. Oil Chem. Soc., 50:400–403 (1973).
G. Rakow, Z. Pflanzenzuchtg, 69, 62–82 (1973).
Robbelen et al., International Conference on the Science, Technology and Marketing of Rapeseed and Rapeseed Products, Sept. 20–23, 1970.
Gerhard Robbelen. Biotechnology for the Oils and Fats Industry, 10:97–105, 1984.
Robbelen et al., Z. Pflanzenzuchtg, 75, 93–105 (1975).
Roy et al., Z. Pflanzenzuchtg, 95:201–209 (1985).
Roy et al., Plant Breeding, 98:89–96 (1987).
Scarth et al., Can. J. Plant Sci., 68–509–511 (1988).
V.I. Shpota, Proceedings of the International Rapeseed Conference, Poznan, Poland, pp. 560–565 (May 1987).
Topfer et al., Science, 268:681–686 (1995).
Yadav et al., Plant Physiol., 103:467–476 (1993).

*Primary Examiner*—Elizabeth C. Kemmerer
*Attorney, Agent, or Firm*—Fish & Richardson P.C., P.A.

[57] ABSTRACT

An endogenous oil extracted from Brassica seeds is disclosed that contains, after crushing and extraction, greater than 86% oleic acid and less than 2.5% α-linolenic acid. The oil also contains less than 7% linoleic acid. The Brassica seeds are produced by plants that contain seed-specific inhibition of microsomal oleate desaturase and microsomal linoleate desaturase gene expression. Such inhibition can be created by cosuppression or antisense technology. Such an oil has a very high oxidative stability in the absence of added antioxidants.

23 Claims, No Drawings

CANOLA OIL HAVING INCREASED OLEIC ACID AND DECREASED LINOLENIC ACID CONTENT

TECHNICAL FIELD

This invention relates to a Brassica canola oil having an elevated oleic acid content and a decreased linolenic acid profile in the seed oil. The invention also relates to methods by which such an oil may be produced.

BACKGROUND OF THE INVENTION

Diets high in saturated fats increase low density lipoproteins (LDL) which mediate the deposition of cholesterol on blood vessels. High plasma levels of serum cholesterol are closely correlated with atherosclerosis and coronary heart disease (Conner et al., Coronary Heart Disease: Prevention, Complications, and Treatment, pp. 43–64, 1985). By producing oilseed Brassica varieties with reduced levels of individual and total saturated fats in the seed oil, oil-based food products which contain less saturated fats can be produced. Such products will benefit public health by reducing the incidence of atherosclerosis and coronary heart disease.

The dietary effects of monounsaturated fats have also been shown to have dramatic effects on health. Oleic acid, the only monounsaturated fat in most edible vegetable oils, lowers LDL as effectively as linoleic acid, but does not affect high density lipoproteins (HDL) levels (Mattson, F. H., J. Am. Diet. Assoc., 89:387–391, 1989; Mensink et al., New England J. Med., 321:436–441, 1989). Oleic acid is at least as effective in lowering plasma cholesterol as a diet low in fat and high in carbohydrates (Grundy, S. M., New England J. Med., 314:745–748, 1986; Mensink et al., New England J. Med., 321:436–441, 1989). In fact, a high oleic acid diet is preferable to low fat, high carbohydrate diets for diabetics (Garg et al., New England J. Med., 319:829–834, 1988). Diets high in monounsaturated fats are also correlated with reduced systolic blood pressure (Williams et al., J. Am. Med. Assoc., 257:3251–3256, 1987). Epidemiological studies have demonstrated that the "Mediterranean" diet, which is high in fat and monounsaturates, is not associated with coronary heart disease.

Intensive breeding has produced Brassica plants whose seed oil contains less than 2% erucic acid. The same varieties have also been bred so that the defatted meal contains less than 30 µmol glucosinolates/gram. Brassica seeds, or oils extracted from Brassica seeds, that contain less than 2% erucic acid ($C_{22:1}$), and produce a meal with less than 30 µmol glucosinolates/gram are referred to as canola seeds or canola oils. Plant lines producing such seeds are also referred to as canola lines or varieties.

Many breeding studies have been directed to alteration of the fatty acid composition in seeds of Brassica varieties. For example, Pleines and Freidt, Fat Sci. Technol., 90(5), 167–171 (1988) describe plant lines with reduced $C_{18:3}$ levels (2.5–5.8%) combined with high oleic content (73–79%). Roy and Tarr, Z. Pflanzenzuchtg, 95(3), 201–209 (1985) teaches transfer of genes through an interspecific cross from Brassica juncea into Brassica napus resulting in a reconstituted line combining high linoleic with low linolenic acid content. Roy and Tarr, Plant Breeding, 98, 89–96 (1987) discuss prospects for development of B. napus L. having improved linoleic and linolenic acid content. Canvin, Can. J. Botany, 43, 63–69 (1965) discusses the effect of temperature on the fatty acid composition of oils from several seed crops including rapeseed.

Mutations can be induced with extremely high doses of radiation and/or chemical mutagens (Gaul, H. Radiation Botany (1964) 4:155–232). High dose levels which exceed LD50, and typically reach LD90, led to maximum achievable mutation rates. In mutation breeding of Brassica varieties, high levels of chemical mutagens alone or combined with radiation have induced a limited number of fatty acid mutations (Rakow, G. Z. Pflanzenzuchtg (1973) 69:62–82).

Rakow and McGregor, J. Amer. Oil Chem. Soc., 50, 400–403 (October 1973) discuss problems associated with selecting mutants affecting seed linoleic and linolenic acid levels. The low α-linolenic acid mutation derived from the Rakow mutation breeding program did not have direct commercial application because of low seed yield. The first commercial cultivar using the low α-linolenic acid mutation derived in 1973 was released in 1988 as the variety Stellar (Scarth, R. et al., Can. J. Plant Sci. (1988) 68:509–511).

The α-linolenic acid content of Stellar seeds was greater than 3% and the linoleic acid content was about 28%.

Chemical and/or radiation mutagenesis has been used in an attempt to develop an endogenous canola oil having an oleic acid content of greater than 79% and an α-linolenic acid content of less than 5%. Wong, et al., EP 0 323 753 B1. However, the lowest α-linolenic acid level achieved was about 2.7%. PCT publication WO 91/05910 discloses mutagenesis of a starting Brassica napus line in order to increase the oleic acid content in the seed oil. However, the oleic acid content in canola oil extracted from seeds of such mutant lines did not exceed 80%.

The quality of canola oil and its suitability for different end uses is in large measure determined by the relative proportion of the various fatty acids present in the seed triacylglycerides. As an example, the oxidative stability of canola oil, especially at high temperatures, decreases as the proportion of tri-unsaturated acids increases. Oxidative stability decreases to a lesser extent as the proportion of di-unsaturated acids increases. However, it has not been possible to alter the fatty acid composition in Brassica seeds beyond certain limits. Thus, an endogenous canola oil having altered fatty acid compositions in seeds is not available for certain specialty uses. Instead, such specialty oils typically are prepared from canola oil by further processing, such as hydrogenation and/or fractionation.

SUMMARY OF THE INVENTION

An endogenous oil obtained from Brassica seeds is disclosed. The oil has an oleic acid content of greater than about 80%, an α-linolenic acid content of less than about 2.5% and an erucic acid content of less than about 2%, which contents are determined after hydrolysis of the oil. Preferably the oleic acid content is from about 84% to about 88% and the α-linolenic acid content is from about 1% to about 2%. The oil may further have a linoleic acid content of from about 1% to about 10%, also determined after hydrolysis of the oil. The oil can be obtained from Brassica napus seeds, for example.

Also disclosed herein is a Brassica plant containing at least one recombinant nucleic construct. The construct(s) comprise a first seed-specific regulatory sequence fragment operably linked to a wild-type microsomal delta-12 fatty acid desaturase coding sequence fragment and a second seed-specific regulatory sequence fragment operably linked to a wild-type microsomal delta-15 fatty acid desaturase coding sequence fragment. Such a plant produces seeds that yield an oil having an oleic acid content of about 86% or greater and an erucic acid content of less than about 2%, which are determined after hydrolysis of the oil. In some embodiments, the plant contains first and second recombinant nucleic acid constructs, the first construct comprising the delta-12 desaturase coding sequence fragment and the second recombinant nucleic acid construct comprising the delta-15 desaturase coding sequence fragment. The delta-12 or delta-15 desaturase coding sequence fragments may comprise either a partial or a full-length Brassica delta-12 or delta-15 desaturase coding sequence.

Another Brassica plant containing at least one recombinant nucleic acid construct is disclosed herein. The construct(s) comprises a first seed-specific regulatory sequence fragment operably linked to a wild-type microsomal delta-12 fatty acid desaturase coding sequence fragment and a second seed-specific regulatory sequence fragment operably linked to a wild-type microsomal delta-15 fatty acid desaturase coding sequence fragment. The plant produces seeds yielding an oil having an oleic acid content of 80% or greater, an α-linolenic acid content of about 2.5% or less and an erucic acid content of less than about 2%, which contents are determined after hydrolysis of the oil. Such a plant may have first and second regulatory sequence fragments linked in sense orientation to the delta-12 and delta-15 desaturase coding sequence fragments, respectively. Alternatively the first and second regulatory sequence fragments may be linked in antisense orientation to the corresponding coding sequence fragments. The delta-12 or delta-15 desaturase coding sequence fragments may comprise a partial or a full-length Brassica delta-12 or delta-15 desaturase coding sequence. The plant may produce seeds yielding an oil having an oleic acid content of 80% or greater, an α-linolenic acid content of about 2.5% or less and an erucic acid content of less than about 2%, which contents are determined after hydrolysis of the oil.

A method of producing an endogenous oil from Brassica seeds is disclosed herein. The method comprises the steps of: creating at least one Brassica plant having a seed-specific reduction in microsomal delta-12 fatty acid desaturase gene expression and a seed-specific reduction in microsomal delta-15 fatty acid desaturase gene expression; crushing seeds produced from the plant; and extracting the oil from the seeds. The oil has an oleic acid content of about 86% or greater and an erucic acid content of less than about 2%, determined after hydrolysis of the oil. The seed-specific reduction in delta-12 or delta-15 desaturase expression may be created by cosuppression or antisense.

Another method of producing an endogenous oil from Brassica seeds is disclosed herein. The method comprises the steps of: creating at least one Brassica plant having a seed-specific reduction in microsomal delta-12 fatty acid desaturase gene expression and a seed-specific reduction in microsomal delta-15 fatty acid desaturase gene expression; crushing seeds produced from the plant; and extracting the oil from the seeds. The oil has an oleic acid content of about 80% or greater, an α-linolenic acid content of 2.5% or less and an erucic acid content of less than about 2%, determined after hydrolysis of the oil. The seed-specific reduction in delta-12 or delta-15 desaturase expression may be created by cosuppression or by antisense.

DESCRIPTION OF THE PREFERRED EMBODIMENTS

The term "fatty acid desaturase" refers to an enzyme which catalyzes the breakage of a carbon-hydrogen bond and the introduction of a carbon-carbon double bond into a fatty acid molecule. The fatty acid may be free or esterified to another molecule including, but not limited to, acyl-carrier protein, coenzyme A, sterols and the glycerol moiety of glycerolipids. The term "glycerolipid desaturases" refers to a subset of the fatty acid desaturases that act on fatty acyl moieties esterified to a glycerol backbone. "Delta-12 desaturase" refers to a fatty acid desaturase that catalyzes the formation of a double bond between carbon positions 6 and 7 (numbered from the methyl end), (i.e., those that correspond to carbon positions 12 and 13 (numbered from the carbonyl carbon) of an 18 carbon-long fatty acyl chain. "Delta-15 desaturase" refers to a fatty acid desaturase that catalyzes the formation of a double bond between carbon positions 3 and 4 (numbered from the methyl end), (i.e., those that correspond to carbon positions 15 and 16 (numbered from the carbonyl carbon) of an 18 carbon-long fatty acyl chain. "Microsomal desaturase" refers to the cytoplasmic location of the enzyme, while "chloroplast desaturase" and "plastid desaturase" refer to the plastid location of the enzyme. It should be noted that these fatty acid desaturases have never been isolated and characterized as proteins. Accordingly, the terms such as "delta-12 desaturase" and "delta-15 desaturase" are used as a convenience to describe the proteins encoded by nucleic acid fragments that have been isolated based on the phenotypic effects caused by their disruption. They do not imply any catalytic mechanism. For example, delta-12 desaturase refers to the enzyme that catalyzes the formation of a double bond between carbons 12 and 13 of an 18 carbon fatty acid irrespective of whether it "counts" the carbons from the methyl, carboxyl end, or the first double bond.

Microsomal delta-12 fatty acid desaturase (also known as omega-6 fatty acid desaturase, cytoplasmic oleic desaturase or oleate desaturase) is involved in the enzymatic conversion of oleic acid to linoleic acid. A microsomal delta-12 desaturase has been cloned and characterized using T-DNA tagging. Okuley, et al., Plant Cell 6:147–158 (1994). The nucleotide sequences of higher plant genes encoding microsomal delta-12 fatty acid desaturase are described in Lightner et al., WO94/11516.

Microsomal delta-15 fatty acid desaturase (also known as omega-3 fatty acid desaturase, cytoplasmic linoleic acid desaturase or linoleate desaturase) is involved in the enzymatic conversion of linoleic acid to α-linolenic acid. Sequences of higher plant genes encoding microsomal and plastid delta-15 fatty acid desaturases are disclosed in Yadav, N., et al., Plant Physiol., 103:467–476 (1993), WO 93/11245 and Arondel, V. et al., Science, 258:1353–1355 (1992).

Brassica species have more than one gene for endogenous microsomal delta-12 desaturase and more than one gene for endogenous microsomal delta-15 desaturase. The genes for microsomal delta-12 desaturase are designated Fad2 while the genes for microsomal delta-1s desaturase are designated Fad3. In amphidiploids, each gene is derived from one of the ancestral genomes making up the species under consideration. The full-length coding sequences for the wild-type Fad2 genes from *Brassica napus* (termed the D form and the F form) are shown in SEQ ID NO:5 and SEQ ID NO:1, respectively. The full-length coding sequence for a wild-type Fad3 gene is disclosed in WO 93/11245.

The inventors have discovered canola oils that have novel fatty acid compositions, e.g., very high oleic acid levels and very low α-linolenic acid levels. Such oils may be obtained by crushing seeds of transgenic Brassica plants exhibiting a seed-specific reduction in delta-12 desaturase and delta-15 desaturase activity; oil of the invention is extracted therefrom. Expression of Fad2 and Fad3 in seeds is reduced such that the resulting seed oil possesses very high levels of oleic acid and very low levels of α-linolenic acid. The fatty acid composition of the endogenous seed oil, as determined after hydrolysis of fatty acid esters reflects the novel fatty acid composition of such seeds.

The fatty acid composition of oils disclosed herein is determined by techniques known to the skilled artisan, e.g., hydrolysis of esterified fatty acids (triacylglycerides and the like) in a bulk seed sample followed by gas-liquid chromatography (GLC) analysis of fatty acid methyl esters.

In one embodiment, an oil of the invention has an oleic acid content of about 80% or greater, as well as a surprisingly low α-linolenic acid content of about 2.5% or less. The oleic acid content is preferably from about 84% to about 89%, more preferably from about 86% to about 89%. The α-linolenic acid preferably is from about 1% to less than about 2.5%, more preferably from about 1% to about 2%.

The linoleic acid content of an oil of this embodiment typically is less than about 10%, preferably less than about 7%, more preferably from about 2% to about 6%.

Canola seed is crushed by techniques known in the art. The seed typically is tempered by spraying the seed with water to raise the moisture to, for example, 8.5%. The tempered seed is flaked using smooth roller with, for example, a gap setting of 0.23 to 0.27 mm. Heat may be applied to the flakes to deactivate enzymes, facilitate further cell rupturing, coalesce the oil droplets and agglomerate protein particles in order to ease the extraction process.

Typically, oil is removed from the heated canola flakes by a screw press to press out a major fraction of the oil from the flakes. The resulting press cake contains some residual oil.

Crude oil produced from the pressing operation typically is passed through a settling tank with a slotted wire drainage top to remove the solids expressed out with the oil in the screw pressing operation. The clarified oil can be passed through a plate and frame filter to remove the remaining fine solid particles.

Canola press cake produced from the screw pressing operation can be extracted with commercial n-Hexane. The canola oil recovered from the extraction process is combined with the clarified oil from the screw pressing operation, resulting in a blended crude oil.

Free fatty acids and gums typically are removed from the crude oil by heating in a batch refining tank to which food grade phosphoric acid has been added. The acid serves to convert the non-hydratable phosphatides to a hydratable form, and to chelate minor metals that are present in the crude oil. The phosphatides and the metal salts are removed from the oil along with the soapstock. The oil-acid mixture is treated with sodium hydroxide solution to neutralize the free fatty acids and the phosphoric acid in the acid-oil mixture. The neutralized free fatty acids, phosphatides, etc. (soapstock) are drained off from the neutralized oil. A water wash may be done to further reduce the soap content of the oil. The oil may be bleached and deodorized before use, if desired, by techniques known in the art.

A transgenic plant disclosed herein contains at least one recombinant nucleic acid construct. The construct or constructs comprise an oleate desaturase coding sequence fragment and a linoleate desaturase coding sequence fragment, both of which are expressed preferentially in developing seeds. Seed-specific expression of the recombinant desaturases results in a seed-specific reduction in native desaturase gene expression. The seed-specific defect in delta-12 and delta-15 desaturase gene expression alters the fatty acid composition in mature seeds produced on the plant, so that the oil obtained from such seeds has the novel fatty acid compositions disclosed herein.

Typically, the oleate and linoleate desaturase sequence fragments are present on separate constructs and are introduced into the non-transgenic parent on separate plasmids. The desaturase fragments may be isolated or derived from, e.g., Brassica spp., soybean (*Glycine max*), sunflower and Arabidopsis. Preferred host or recipient organisms for introduction of a nucleic acid construct are oil-producing species, such as *Brassica napus, B. rapa* and *B. juncea*.

A transgenic plant disclosed herein preferably is homozygous for the transgene containing construct. Such a plant may be used as a parent to develop plant lines or may itself be a member of a plant line, i.e., be one of a group of plants that display little or no genetic variation between individuals for the novel oil composition trait. Such lines may be created by several generations of self-pollination and selection, or vegetative propagation from a single parent using tissue or cell culture techniques. Other means of breeding plant lines from a parent plant are known in the art.

Progeny of a transgenic plant are included within the scope of the invention, provided that such progeny exhibit the novel seed oil characteristics disclosed herein. Progeny of an instant plant include, for example, seeds formed on $F_1$, $F_2$, $F_3$, and subsequent generation plants, or seeds formed on $BC_1$, $BC_2$, $BC_3$ and subsequent generation plants.

A seed-specific reduction in Fad2 and Fad3 gene expression may be achieved by techniques including, but not limited to, antisense and cosuppression. These phenomena significantly reduce expression of the gene product by the native genes (wild-type or mutated). The reduction in gene expression can be inferred from the decreased level of reaction product and the increased level of substrate in seeds (e.g., decreased 18:2 and increased 18:1), compared to the corresponding levels in plant tissues expressing the native genes.

The preparation of antisense and cosuppression constructs for inhibition of fatty acid desaturases may utilize fragments containing the transcribed sequence for the Fad2 and Fad3 fatty acid desaturase genes in canola. These genes have been cloned and sequenced as discussed hereinabove.

Antisense RNA has been used to inhibit plant target genes in a tissue-specific manner. van der Krol et al., Biotechniques 6:958–976 (1988). Antisense inhibition has been shown using the entire cDNA sequence as well as a partial cDNA sequence. Sheehy et al., Proc. Natl. Acad. Sci. USA 85:8805–8809 (1988); Cannon et al., Plant Mol. Biol. 15:39–47 (1990). There is also evidence that 3' non-coding sequence fragment and 5' coding sequence fragments, containing as few as 41 base-pairs of a 1.87 kb cDNA, can play important roles in antisense inhibition. (Ch'ng et al., Proc. Natl. Acad. Sci. USA 86:10006–10010 (1989); Cannon et al., supra.

The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known. Napoli et al., The Plant Cell 2:279–289 (1990); van der Krol et al., The Plant Cell 2:291–299 (1990); Smith et al., Mol. Gen. Genetics 224:477–481 (1990).

Nucleic acid fragments comprising a partial or a full-length delta-12 or delta-15 fatty acid desaturase coding sequence are operably linked to at least one suitable regulatory sequence in antisense orientation (for antisense constructs) or in sense orientation (for cosuppression constructs). Molecular biology techniques for preparing such chimeric genes are known in the art. The chimeric gene is introduced into a Brassica plant and transgenic progeny displaying a fatty acid composition disclosed herein due to antisense or cosuppression are identified. Transgenic plants that produce a seed oil having a fatty acid composition disclosed herein are selected for use in the invention. Experimental procedures to develop and identify cosuppressed plants involve breeding techniques and fatty acid analytical techniques known in the art.

One may use a partial cDNA sequence for cosuppression as well as for antisense inhibition. For example, cosuppression of delta-12 desaturase and delta-15 desaturase in *Brassica napus* may be achieved by expressing, in the sense orientation, the entire or partial seed delta-12 desaturase cDNA found in pCF2-165D. See WO 94/11516.

Seed-specific expression of native Fad2 and Fad3 genes can also be inhibited by non-coding regions of an introduced copy of the gene. See, e.g., Brusslan, J. A. et al. (1993) Plant Cell 5:667–677; Matzke, M. A. et al., Plant Molecular Biology 16:821–830). One skilled in the art can readily isolate genomic DNA containing sequences that flank desaturase coding sequences and use the non-coding regions for antisense or cosuppression inhibition.

Regulatory sequences typically do not themselves code for a gene product. Instead, regulatory sequences affect the expression level of the mutant coding sequence. Examples of regulatory sequences are known in the art and include, without limitation, promoters of genes expressed during embryogenesis, e.g., a napin promoter, a phaseolin promoter, a oleosin promoter and a cruciferin promoter. Native regulatory sequences, including the native promoters, of delta-12 and delta-15 fatty acid desaturase genes can be readily isolated by those skilled in the art and used in constructs of the invention. Other examples of suitable regulatory sequences include enhancers or enhancer-like elements, introns and 3' non-coding regions such as poly A sequences. Further examples of suitable regulatory sequences for the proper expression of mutant or wild-type delta-12 or mutant delta-15 coding sequences are known in the art.

In preferred embodiments, regulatory sequences are seed-specific, i.e., the chimeric desaturase gene product is preferentially expressed in developing seeds and expressed at low levels or not at all in the remaining tissues of the plant. Seed-specific regulatory sequences preferably stimulate or induce expression of the recombinant desaturase coding sequence fragment at a time that coincides with or slightly precedes expression of the native desaturase gene. Murphy et al., J. Plant Physiol. 135:63–69 (1989).

Transgenic plants for use in the invention are created by transforming plant cells of Brassica species. Such techniques include, without limitation, Agrobacterium-mediated transformation, electroporation and particle gun transformation. Illustrative examples of transformation techniques are described in U.S. Pat. No. 5,204,253, (particle gun) and U.S. Pat. No. 5,188,958 (Agrobacterium), incorporated herein by reference. Transformation methods utilizing the Ti and Ri plasmids of Agrobacterium spp. typically use binary type vectors. Walkerpeach, C. et al., in Plant Molecular Biology Manual, S. Gelvin and R. Schilperoort, eds., Kluwer Dordrecht, C1:1–19 (1994). If cell or tissue cultures are used as the recipient tissue for transformation, plants can be regenerated from transformed cultures by techniques known to those skilled in the art.

One or more recombinant nucleic acid constructs, suitable for antisense or cosuppression of native Fad2 and Fad3 genes are introduced, and at least one transgenic Brassica plant is obtained. Seeds produced by the transgenic plant(s) are grown and either selfed or outcrossed to obtain plants homozygous for the recombinant construct. Seeds are analyzed as discussed above in order to identify those homozygotes having native fatty acid desaturase activities inhibited by the mechanisms discussed above. Homozygotes may be entered into a breeding program, e.g., to increase seed, to introgress the novel oil composition trait into other lines or species, or for further selection of other desirable traits (disease resistance, yield and the like).

Fatty acid composition is followed during the breeding program by analysis of a bulked seed sample or of a single half-seed. Half-seed analysis is useful because the viability of the embryo is maintained and thus those seeds having a desired fatty acid profile may be advanced to the next generation. However, half-seed analysis is also known to be an inaccurate representation of the genotype of the seed being analyzed. Bulk seed analysis typically yields a more accurate representation of the fatty acid profile in seeds of a given genotype.

Procedures for analysis of fatty acid composition are known in the art. These procedures can be used to identify individuals to be retained in a breeding program; the procedures can also be used to determine the product specifications of commercial or pilot plant oils.

The relative content of each fatty acid in canola seeds can be determined either by direct trans-esterification of individual seeds in methanolic $H_2SO_4$ (2.5%) or by hexane extraction of bulk seed samples followed by trans-esterification of an aliquot in 1% sodium methoxide in methanol. Fatty acid methyl esters can be extracted from the methanolic solutions into hexane after the addition of an equal volume of water.

For example, a seed sample from each transformant in a breeding program is crushed with a mortar and pestle and extracted 4 times with 8 mL hexane at about 50° C. The extracts from each sample are reduced in volume and two aliquots are taken for esterification. Separation of the fatty acid methyl esters can be carried out by gas-liquid chromatography using an Omegawax 320 column (Supelco Inc., 0.32 mm ID×30M) run isothermally at 220° and cycled to 260° between each injection.

Alternatively, seed samples from a breeding program are ground and extracted in methanol/KOH, extracted with iso-octane, and fatty acids separated by gas chromatography.

A method to produce an oil of the invention comprises the creation of at least one Brassica plant having a seed-specific reduction in Fad2 and Fad3 gene expression, as discussed above. Seeds produced by such a plant, or its progeny, are crushed and the oil is extracted from the crushed seeds. Such lines produce seeds yielding an oil of the invention, e.g., an oil having from about 80% to about 88% oleic acid, from about 1% to about 2% α-linolenic acid and less than about 2% erucic acid.

Alternatively, such a plant can be created by crossing two parent plants, one exhibiting a reduction in Fad2 gene expression and the other exhibiting a reduction in Fad3 gene expression. Progeny of the cross are outcrossed or selfed in order to obtain progeny seeds homozygous for both traits.

Transgenic plants having a substantial reduction in Pad2 and Fad3 gene expression in seeds have novel fatty acid profiles in oil extracted from such seeds, compared to known canola plants, e.g., the reduction in both desaturase activities results in a novel combination of high oleic and lower α-linolenic acid in seed oils. By combining seed-specific inhibition of microsomal delta-12 desaturase with seed-specific inhibition of microsomal delta-15, one obtains very low levels of seed α-linolenic acid, without adversely affecting agronomic properties.

It is noteworthy that Fad2 and Fad3 cosuppression constructs provide a novel means for producing canola oil having 86% oleic acid or greater. A method of producing a canola oil having greater than 86% oleic acid comprises the creation of a transgenic Brassica plant containing at least one recombinant nucleic acid construct, which construct(s) comprises an oleate desaturase coding sequence expressed preferentially in developing seeds and a linoleate desaturase coding sequence expressed preferentially in developing seeds. A proportion of the plants that are homozygous for the transgenes have seed-specific cosuppression of the native linoleate desaturase. Seeds produced by such transgenic cosuppressed plants are crushed and the oil is extracted therefrom. The oil has about 86% or greater oleic acid and less than about 2% erucic acid. The oleic acid content can be as high as 89%.

Transgenic plants exhibiting cosuppression of Fad2 and Fad3 produce seeds having a very high oleic acid content. This result was unexpected because it was not known if one could obtain plants in which inhibition of Fad2 and Fad3 via cosuppression was sufficient to achieve an oleic acid level of 86% or greater in seeds. Indeed, it was not known if two cosuppressed genes in fatty acid metabolism could be introduced in canola without the first cosuppression gene interfering with the second cosuppression gene, or without adversely affecting other agronomic traits.

Marker-assisted breeding techniques may be used to identify and follow a desired fatty acid composition during the breeding process. Such markers may include RFLP, RAPD, or PCR markers, for example. Marker-assisted breeding techniques may be used in addition to, or as an alternative to, other sorts of identification techniques. An example of marker-assisted breeding is the use of PCR primers that specifically amplify the junction between a promoter fragment and the coding sequence of a Fad2 gene.

While the invention is susceptible to various modifications and alternative forms, certain specific embodiments thereof are described in the general methods and examples set forth below. For example the invention may be applied to all Brassica species, including *B. rapa, B. juncea*, and *B. hirta*, to produce substantially similar results. It should be understood, however, that these examples are not intended to limit the invention to the particular forms disclosed. Instead, the disclosure is to cover all modifications, equivalents and alternatives falling within the scope of the invention.

EXAMPLE 1

CONSTRUCTS FOR COSUPPRESSION OF DELTA-12 FATTY ACID DESATURASE AND DELTA-15 FATTY ACID DESATURASE

The wild-type Brassica cDNA coding sequence for the delta-12 desaturase D form was cloned as described in WO 94/11516, which is incorporated herein by reference. Briefly, rapeseed cDNAs encoding cytoplasmic oleate (18:1) desaturase were obtained by screening a cDNA library made from developing rapeseed using a heterologous probe derived from an Arabidopsis cDNA fragment encoding the same enzyme. (Okuley et al 1994). The full-length coding sequence of Fad2 is found as SEQ ID NO:5. Rapeseed cDNAs encoding the cytoplasmic linoleate (18:2) desaturase (Fad3) were obtained as described in WO 93/11245, incorporated herein by reference. See also (Yadav et. al 1993). Seed specific expression of these cDNAs in transgenic rapeseed was driven by one of four different seed storage protein promoters, napin, oleosin and cruciferin promoters from *B. napus* and a phaseolin promoter from *Phaseolus vulgaris*.

Detailed procedures for manipulation of DNA fragments by restriction endonuclease digestion, size separation by agarose gel electrophoresis, isolation of DNA fragments from agarose gels, ligation of DNA fragments, modification of cut ends of DNA fragments and transformation of *E. coli* cells with plasmids have been described. Sambrook et al., (Molecular Cloning, A Laboratory Manual, 2nd ed (1989) Cold Spring Harbor Laboratory Press); Ausubel et al., Current Protocols in Molecular Biology (1989) John Wiley & Sons). Plant molecular biology procedures are described in Plant Molecular Biology Manual, Gelvin S. and Schilperoort, R. eds. Kluwer, Dordrecht (1994).

The plasmid pZS212 was used to construct binary vectors for these experiments. pZS212 contains a chimeric CaMV35S/NPT gene for use in selecting kanamycin resistant transformed plant cells, the left and right border of an Agrobacterium Ti plasmid T-DNA, the *E. coli lacZ* α-complementing segment with unique restriction endonuclease sites for EcoRI, KpnI, BamHI and SalI, the bacterial replication origin from the Pseudomonas plasmid pVS1 and a bacterial Tn5 NPT gene for selection of transformed Agrobacterium. See WO 94/11516, p. 100.

The first construct was prepared by inserting a full-length mutant Brassica Fad2 D gene coding sequence fragment in sense orientation between the phaseolin promoter and phaseolin 3' poly A region of plasmid pCW108. The full-length coding sequence of the mutant gene is found in SEQ ID NO:3.

The pCW108 vector contains the bean phaseolin promoter and 3' untranslated region and was derived from the commercially available pUC18 plasmid (Gibco-BRL) via plasmids AS3 and pCW104. Plasmid AS3 contains 495 base pairs of the *Phaseolus vulgaris* phaseolin promoter C75 seed storage protein starting followed by the entire 1175 base pairs of the 3' untranslated region of the same gene. Sequence descriptions of the 7S seed storage protein promoter are found in Doyle et al., J. Biol. Chem. 261:9228–9238 (1986) and Slightom et al., Proc. Natl. Acad. Sci. USA, 80:1897–1901 (1983). Further sequence description may be found in WO 91/13993. The fragment was cloned into the Hind III site of pUC18. The additional cloning sites of the pUC18 multiple cloning region (Eco RI, Sph I, Pst I and Sal I) were removed by digesting with Eco RI and Sal I, filling in the ends with Klenow and religating to yield the plasmid pCW104. A new multiple cloning site was created between the 495bp of the 5' phaseolin and the 1175bp of the 3' phaseolin by inserting a dimer of complementary synthetic oligonucleotides to create the plasmid pCW108. See WO 94/11516. This plasmid contains unique Nco I, Sma I, Kpn I and Xba I sites directly behind the phaseolin promoter.

The phaseolin promoter:mutantFad2:phaseolin poly A construct in pCW108 was excised and cloned between the SalI/EcoRI sites of pZS212. The resulting plasmid was designated pIMC201.

A second plasmid was constructed by inserting the full-length wild type Brassica Fad2 D gene coding sequence into the NotI site of plasmid pIMC401, which contains a 2.2 kb napin expression cassette. See, e.g., WO94/11516, page 102. The 5'-napin:Fad2:napin poly A-3' construct was inserted into the SalI site of pZS212 and the resulting 17.2 Kb plasmid was termed pIMC127. Napin promoter sequences are also disclosed in U.S. Pat. No. 5,420,034.

A third plasmid, pIMC135, was constructed in a manner similar to that described above for pIMC127. Plasmid pIMC135 contains a 5' cruciferin promoter fragment operably linked in sense orientation to the full-length wild-type Brassica Fad2 D gene coding sequence, followed by a cruciferin 3' poly A fragment. The 5'-cruciferin:Fad2 D:cruciferin polyA cassette was inserted into pZS212; the resulting plasmid was termed pIMC135. Suitable cruciferin regulatory sequences are disclosed in Rodin, J. et al., J. Biol. Chem. 265:2720 (1990); Ryan, A. et al., Nucl. Acids Res. 17:3584 (1989) and Simon, A. et al., Plant Mol. Biol. 5:191 (1985). Suitable sequences are also disclosed in the Genbank computer database, e.g., Accession No. M93103.

A fourth plasmid, pIMC133 was constructed in a manner similar to that described above. Plasmid pIMC133 contains a 5' oleosin promoter fragment operably linked in sense orientation to the full-length Brassica Fad2 D gene coding sequence, followed by a 3' oleosin poly A fragment. See, e.g., WO 93/20216, incorporated herein by reference.

A napin-Fad3 construct was made by first isolating a delta-15 desaturase coding sequence fragment from pBNSF3-f2. The fragment contained the full-length coding sequence of the desaturase, disclosed as SEQ ID NO: 6 in WO 93/11245, incorporated herein by reference. The 1.2 kb fragment was fitted with linkers and ligated into pIMC401. The 5' napin:Fad3:3' napin cassette was inserted into the Sal I site of pZS212; the resulting plasmid was designated pIMC110.

EXAMPLE 2

CREATION OF TRANSGENIC COSUPPRESSED PLANTS

The plasmids pIMC201, pIMC127, pIMC135, pIMC133 and pIMC110 were introduced into Agrobacterium strain LBA4404/pAL4404 by a freeze-thaw method. The plasmids were introduced into *Brassica napus* cultivar Westar by the method of Agrobacterium-mediated transformation as described in WO94/11516, incorporated herein by reference. Transgenic progeny plants containing pIMC201 were designated as the WS201 series. Plants transformed with pIMC127 were designated as the WS687 series. Plants transformed with pIMC135 were designated as the WS691 series. Plants transformed with pIMC133 were designated as the WS692 series. Plants transformed with pIMC110 were designated as the WS663 series.

Unless indicated otherwise, fatty acid percentages described herein are percent by weight of the oil in the indicated seeds as determined after extraction and hydrolysis.

From about 50 to 350 transformed plants (T1 generation) were produced for each cDNA and promoter combination. T1 plants were selfed to obtain T2 seed. T2 samples in which cosuppression events occurred were identified from the fatty acid profile and from the presence of the transgene by molecular analysis. The transformed plants were screened for phenotype by analysis of the relative fatty acid contents of bulk seed from the first transformed generation by GC separation of fatty acid methyl esters.

T2 seed was sown in 4-inch pots containing Pro-Mix soil. The plants, along with Westar controls, were grown at 25°±3° C.,/18°±3° C., 14/10 hr day/night conditions in the greenhouse. At flowering, the terminal raceme was self-pollinated by bagging. At maturity, seed was individually harvested from each plant, labelled, and stored to ensure that the source of the seed was known.

Fatty acid profiles were determined as described in WO 91/05910. For chemical analysis, 10-seed bulk samples were hand ground with a glass rod in a 15-mL polypropylene tube and extracted in 1.2 mL 0.25 N KOH in 1:1 ether/methanol. The sample was vortexed for 30 sec. and heated for 60 sec. in a 60° C. water bath. Four mL of saturated NaCl and 2.4 mL of iso-octane were added, and the mixture was vortexed again. After phase separation, 600 µL of the upper organic phase were pipetted into individual vials and stored under nitrogen at −5° C. One µL samples were injected into a Supelco SP-2330 fused silica capillary column (0.25 mm ID, 30M length, 0.20 µm df).

The gas chromatograph was set at 180° C. for 5.5 minutes, then programmed for a 2° C./minute increase to 212 °C., and held at this temperature for 1.5 minutes. Total run time was 23 minutes. Chromatography settings were: Column head pressure—15 psi, Column flow (He)—0.7 mL/min., Auxiliary and Column flow—33 mL/min., Hydrogen flow—33 mL/min., Air flow—400 mL/min., Injector temperature—250° C., Detector temperature—300° C., Split vent—1/15.

Table 1 shows the content of the seven major fatty acids in mature seeds from transgenic cosuppressed plants homozygous for the napin:Fad3 construct or the napin:Fad2 construct (T4 or later generation). Overexpression phenotypes and cosuppression phenotypes were observed for both chimeric genes (oleate desaturase and linoleate desaturase); data for plants exhibiting the cosuppression phenotype are shown in the Table.

As shown in Table 1, the homozygous Fad2-cosuppressed seed had a α-linolenic acid content of about 2.9%, which was less than half that of the Westar control; the oleic acid content increased to about 84.1%. The homozygous Fad3-cosuppressed seed had an α-linolenic acid of about 1.2%; the oleic acid and linoleic acid contents in Fad3-cosuppressed plants increased slightly compared to Westar. The results demonstrate that inhibiting gene expression of either enzyme by cosuppression resulted in a change in fatty acid composition of the seed oil.

Fatty Acid Profiles in Oil From Cosuppression Canola Seed

TABLE 1

Fatty Acid Profiles in Oil From Cosuppression Canola Seed

| TRANSGENE CONSTRUCTION | FATTY ACID (% OF TOTAL FATTY ACIDS) | | | | | | | | |
|---|---|---|---|---|---|---|---|---|---|
| | 16:0 | 18:0 | 18:1 | 18:2 | 18:3 | 20:0 | 20:1 | 22:0 | 24:0 |
| non-transformed Westar | 3.9 | 1.8 | 67.0 | 19.0 | 7.5 | 0.6 | 0.8 | 0.6 | 0.1 |
| napin: Fad2 (co-suppression) | 4.3 | 1.4 | 84.1 | 5.2 | 2.9 | 0.6 | 0.9 | 0.5 | 0.2 |
| napin: Fad3 (co-suppression) | 3.8 | 1.5 | 68.5 | 22.1 | 1.2 | 0.6 | 1.1 | 0.4 | 0.1 |

TABLE 2

Fatty Acid Profiles in Oil From Cosuppression Canola Seeds

| Line # | Construct (promoter/ coding sequence) | Fatty Acid Composition | | | | |
|---|---|---|---|---|---|---|
| | | 16:0 | 18:0 | 18:1 | 18:2 | 18:3 |
| 663-40 | napin/Fad3 | 3.9 | 1.4 | 71.2 | 20.1 | 1.2 |
| 687-193 | napin/Fad2 | 4.0 | 1.5 | 82.8 | 5.9 | 3.7 |
| 691-215 | cruciferin/Fad2 | 3.3 | 1.3 | 86.5 | 3.0 | 3.7 |
| 692-090-3 | oleosin/Fad2 | 3.4 | 1.3 | 86.5 | 2.6 | 3.9 |
| 692-105-11 | oleosin/Fad2 | 3.4 | 1.3 | 86.2 | 2.7 | 4.2 |
| 201-389 A23 | phaseolin/MFad2 | 4.2 | 2.7 | 84.6 | 4.7 | 3.7 |

TABLE 3

Range of Fatty Acid Profiles for Fad2 and Fad3 Cosuppression Lines Tested in the Field

| Line No. | Vector | Min/Max | Fatty Acid Composition | | | | |
|---|---|---|---|---|---|---|---|
| | | | C16:0 | C18:0 | C18:1 | C18:2 | C18:3 |
| 663-40 | pIMC110 | Min | 3.5 | 2.3 | 73.5 | 16.3 | 0.8 |
| | | Max | 4.7 | 2.2 | 64.0 | 24.2 | 1.5 |
| 687-193 | pIMC127 | Min | 3.4 | 3.1 | 83.3 | 3.8 | 2.3 |
| | | Max | 3.4 | 2.1 | 85.5 | 3.2 | 2.5 |
| 692-105 | pIMC133 | Min | 3.7 | 2.7 | 84.6 | 2.8 | 2.4 |
| | | Max | 3.3 | 2.3 | 86.3 | 2.1 | 2.7 |
| 691-215 | pIMC135 | Min | 3.2 | 2.4 | 84.6 | 3.0 | 2.5 |
| | | Max | 3.0 | 2.0 | 86.3 | 2.6 | 2.5 |

Table 2 shows the fatty acid profile in T4 or later homozygous seeds produced by six individual plants having various promoter-desaturase gene combinations. The seeds were obtained from greenhouse-grown plants. The results indicate that the oleic acid content ranged from about 82.8% to about 86.5% among the lines carrying the Fad2 constructs. The phaseolin:mutated Fad2 construct was as successful as the wild-type Fad2 constructs in achieving seed-specific Fad2 cosuppression.

The napin:Fad3 cosuppressed plant line had an unusually low α-linolenic acid content of 1.2%. However, the oleic acid content was only 71.2% and the linoleic acid content was similar to that of the non-transformed control Westar in Table 1.

Homozygous seeds from four of the lines in Table 2 were planted in a field nursery in Colorado and self-pollinated. Seed samples from several plants of each line were collected and separately analyzed for fatty acid composition. The results for the 663-40 plant having the minimum and the 663-40 plant having the maximum linolenic acid content observed in the field are shown in Table 3. The results for the 687-193, 692-105 and 691-215 plants having the minimum and maximum oleic acid content in the field are also shown in Table 3.

The results in Table 3 demonstrate that the fatty acid profile in field-grown seeds of cosuppressed transgenic plants was similar to that in the greenhouse-grown seeds (Table 2), indicating that the cosuppression trait confers a stable fatty acid composition on the oil. The results also indicate that an oil having the combination of an oleic acid content of 86% or greater and an α-linolenic acid content of 2.5% or less could not be obtained from plants cosuppressed for either Fad2 or Fad3 alone.

EXAMPLE 3

OIL CONTENT IN SEEDS OF PLANTS EXHIBITING Fad2 and Fad3 COSUPPRESSION

Crosses were made between the napin:Fad3 cosuppressed line 663-40 and three Fad2 cosuppressed lines, 691-215, 692-090-3 and 692-105–11. F1 plants were selfed for 2 generations in the greenhouse to obtain F3 generation seed that was homozygous for both recombinant constructs.

TABLE 4

Fatty Acid Profile in F3 Seeds of
Lines Exhibiting Fad2 and Fad3 Cosuppression

| Line # | Construct | 16:0 | 18:0 | 18:1 | 18:2 | 18:3 |
|---|---|---|---|---|---|---|
| 663-40 | napin/Fad3 | 3.9 | 1.4 | 71.2 | 20.1 | 1.2 |
| 691-215 | cruciferin/Fad2 | 3.9 | 1.3 | 86.5 | 3.0 | 3.7 |
| 663-40X691-215 | napin/Fad3 & cruciferin/Fad2 | 3.2 | 1.4 | 86.2 | 5.2 | 1.5 |
| 663-40 | napin/Fad3 | 3.9 | 1.4 | 71.2 | 20.1 | 1.2 |
| 692-090-3 | oleosin/Fad2 | 3.4 | 1.3 | 86.5 | 2.6 | 3.9 |
| 663-40X692-090-3 | napin/Fad3 & oleosin/Fad2 | 3.4 | 1.5 | 85.5 | 5.0 | 1.7 |
| 663-40 | napin/Fad3 | 3.9 | 1.4 | 71.2 | 20.1 | 1.2 |
| 692-105-11 | oleosin/Fad2 | 3.4 | 1.3 | 86.2 | 2.7 | 4.2 |
| 663-40X692-105-11 | napin/Fad3 & oleosin/Fad2 | 3.4 | 1.4 | 86.8 | 4.6 | 1.4 |

The seed fatty acid profiles of the parent lines and a representative F3 cosuppressed line are shown in Table 4. Plants expressing both cosuppression constructs exhibited an oleic acid level of about 86% or greater. Moreover, this high level of oleic acid was present in combination with an unusually low level of α-linolenic acid, less than 2.0%. However, the linoleic acid content in the F3 seeds increased from about 2.6–3.0% to about 4.6–5.2%.

These results demonstrate that a canola oil can be extracted from rapeseeds that contains greater than 80% oleic acid and less than 2.5% α-linolenic acid. Results similar to those obtained using cosuppression constructs are achieved when antisense constructs are used.

The canola oil extracted from Fad2 and Fad3 cosuppressed F3 seed, or progeny thereof, is found to have superior oxidative stability compared to the oil extracted from Westar seed. The improved oxidative stability of such an oil is measured after refining, bleaching and deodorizing, using the Accelerated Oxygen Method (AOM), American Oil Chemists' Society Official Method Cd 12–57 for fat stability, Active Oxygen Method (revised 1989). The improved oxidative stability is also demonstrated when using the Oxidative Stability Index method. The improved oxidative stability is measured in the absence of added antioxidants.

EXAMPLE 4

OIL CONTENT IN SEEDS OF PLANTS HAVING Fad3 COSUPPRESSION AND CHEMICALLY-INDUCED Fad2 MUTATIONS

Q4275 is a doubly mutagenized B. napus line having defects in the Fad2 gene. Q4275 was derived by chemical mutagenesis of B. napus line IMC129, which carries a mutation in the Fad2 D gene; the coding sequence of the mutated gene is shown in SEQ ID NO:3. Line IMC129 was itself derived by chemical mutagenesis of the cultivar Westar, as disclosed in WO 91/05910. Genetic segregation analysis of crosses between Q4275 and other fatty acid mutant lines indicated that Q4275 carried a mutation in the B. napus Fad2 F gene in addition to the IMC129 Fad2 D gene mutation. Q4275 thus carries chemically induced mutations in both Fad2 genes.

A cross was made between Q4275 and the napin:Fad3 cosuppressed line 663-40. F1 plants were selfed in the greenhouse and F2 plants that were homozygous for the recombinant construct and the Fad2 D and Fad2 F mutated genes were identified by fatty acid profile analysis of the F3 generation seed. After selfing to homozygosity, the fatty acid profiles in seeds of a representative homozygous plant was analyzed and compared to the profile of the parent plants, as shown in Table 5.

The results show that an oil having greater than 87% oleic acid and less than 1.5α-linolenic acid can be obtained from a transgenic Brassica plant containing a seed-specific reduction in Fad3 gene expression as well as chemically-induced mutations in Fad2 genes.

TABLE 5

Fatty Acid Profile of Fad3 Cosuppression, Fad2 Mutated Seeds

|  | 16:0 | 18:0 | 18:1 | 18:2 | 18:3 |
|---|---|---|---|---|---|
| 663-40 | 3.9 | 1.4 | 71.2 | 20.1 | 1.2 |
| Q4275 | 3.3 | 1.5 | 86.7 | 2.2 | 3.1 |
| Q4275 × 663-40 | 3.2 | 1.6 | 87.6 | 4.2 | 1.3 |

TABLE 6

Range of Fatty Acid Profiles for Fad3 Cosuppression,
Fad2 Mutated Lines Tested in the Field

|  |  | 16:0 | 18:0 | 18:1 | 18:2 | 18:3 |
|---|---|---|---|---|---|---|
| 663-40 | Min | 3.5 | 2.3 | 73.5 | 16.3 | 0.8 |
|  | Max | 4.7 | 2.2 | 64.0 | 24.2 | 1.5 |
| Q4275 | Min | 3.2 | 3.3 | 85.0 | 1.8 | 2.0 |
|  | Max | 3.0 | 2.3 | 86.6 | 1.7 | 2.6 |
| Q4275 × 663-40 | Min | 3.2 | 2.0 | 85.1 | 5.3 | 0.9 |
|  | Max | 3.2 | 2.9 | 84.0 | 6.0 | 1.5 |

Additional seed from the homozygous plant described above was planted in the field and self-pollinated. Mature seeds from several progeny plants were separately analyzed for their fatty acid profile. The fatty acid profile for the progeny plant having the minimum linolenic acid content and the plant having the maximum linolenic acid content are shown in Table 6. The results show that the homozygous plant having Fad2 mutations and Fad3 cosuppression had a fatty acid profile in the field that was similar to that of the greenhouse-grown seed (Table 5), indicating that the Fad3 cosuppression trait and the chemically-induced Fad2 mutants conferred a stable fatty acid composition on seeds of this plant. Thus, an oil of the invention can be obtained from either field-grown seeds or greenhouse-grown seeds.

Because of the decreased α-linolenic acid content and increased oleic acid content, an oil of the invention is useful in food and industrial applications. Oils which are low in α-linolenic acid have increased oxidative stability. The rate of oxidation of lipid fatty acids increases with higher levels of linolenic acid leading to off-flavors and off-odors in foods. The present invention provides novel canola oils that are low in α-linolenic acid.

To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A Brassica plant containing at least one recombinant nucleic acid construct, said at least one construct comprising:
   a) a regulatory sequence fragment operably linked to a wild-type microsomal delta-12 fatty acid desaturase coding sequence fragment; and
   b) a regulatory sequence fragment operably linked to a wild-type microsomal delta-15 fatty acid desaturase coding sequence fragment,
said plant exhibiting a seed-specific reduction in native delta-12 and native delta-15 desaturase gene expression, wherein said plant produces seeds yielding an oil having an oleic acid content of about 86% or greater and an erucic acid content of less than about 2%, said oleic acid content and erucic acid content determined after hydrolysis of said oil.

2. The plant of claim 1, wherein said plant contains first and second recombinant nucleic acid constructs, said first construct comprising said delta-12 desaturase coding sequence fragment and said second recombinant nucleic acid construct comprising said delta-15 desaturase coding sequence fragment.

3. The plant of claim 1, wherein said delta-12 desaturase coding sequence fragment comprises a full-length Brassica delta-12 desaturase coding sequence.

4. The plant of claim 1, wherein said delta-15 desaturase coding sequence fragment comprises a full-length Brassica delta-15 desaturase coding sequence.

5. The plant of claim 1, wherein said regulatory sequence fragments are linked in antisense orientation to said delta-12 and delta-15 desaturase coding sequence fragments.

6. A Brassica plant containing at least one recombinant nucleic acid construct, said at least one construct comprising:
   a) a regulatory sequence fragment operably linked to a wild-type microsomal delta-12 fatty acid desaturase coding sequence fragment; and
   b) a regulatory sequence fragment operably linked to a wild-type microsomal delta-15 fatty acid desaturase coding sequence fragment,
said plant exhibiting a seed-specific reduction in native delta-12 and native delta-15 desaturase gene expression, wherein said plant produces seeds yielding an oil having an oleic acid content of 80% or greater, an α-linolenic acid content of about 2.5% or less and an erucic acid content of less than about 2%, said oleic acid content, linolenic acid content and erucic acid content determined after hydrolysis of said oil.

7. The plant of claim 6, wherein said first and second regulatory sequence fragments are linked in sense orientation to said delta-12 and delta-15 desaturase coding sequence fragments, respectively.

8. The plant of claim 6, wherein said plant contains a first recombinant nucleic acid construct comprising said delta-12 desaturase coding sequence fragment and a second recombinant nucleic acid construct comprising said delta-15 desaturase coding sequence fragment.

9. The plant of claim 6, wherein said delta-12 desaturase coding sequence fragment comprises a full-length Brassica delta-12 desaturase coding sequence.

10. The plant of claim 6, wherein said delta-15 desaturase coding sequence fragment comprises a full-length Brassica delta-15 desaturase coding sequence.

11. The plant of claim 6, wherein said plant produces seeds yielding an oil having an oleic acid content of about 84% to about 89%, an α-linolenic acid content of about 1% to about 2% and an erucic acid content of less than about 2%, said oleic acid content, linolenic acid content and erucic acid content determined after hydrolysis of said oil.

12. The plant of claim 11, wherein said oleic acid content is from about 86% to about 89% and said α-linolenic acid content is from about 1% to about 1.7%.

13. The plant of claim 6, wherein said regulatory sequence fragments are linked in antisense orientation to said delta-12 and delta-15 desaturase coding sequence fragments.

14. A method of producing an endogenous oil from Brassica seeds, comprising the steps of:
   a) creating at least one transgenic Brassica plant having a seed-specific reduction in microsomal delta-12 fatty acid desaturase gene expression and a seed-specific reduction in microsomal delta-15 fatty acid desaturase gene expression, wherein said transgenic plant contains at least one recombinant nucleic acid construct, said at least one construct comprising a regulatory sequence fragment operably linked to a wild-type microsomal delta-12 fatty acid desaturase coding sequence fragment and a regulatory sequence fragment operably linked to a wild-type microsomal delta-15 fatty acid desaturase coding sequence fragment;
   b) crushing seeds produced from said plant; and
   c) extracting said oil from said seeds, said oil having an oleic acid content of about 86% or greater and an erucic acid content of less than about 2%, said oleic acid content and erucic acid content determined after hydrolysis of said oil.

15. The method of claim 14, wherein said seed-specific reduction in delta-12 desaturase expression is created by cosuppression.

16. The method of claim 14, wherein said seed-specific reduction in delta-12 desaturase expression is created by antisense suppression.

17. The method of claim 14, wherein said seed-specific reduction in delta-15 desaturase expression is created by cosuppression.

18. The method of claim 14, wherein said seed-specific reduction in delta-15 desaturase expression is created by antisense suppression.

19. A method of producing an endogenous oil from Brassica seeds, comprising the steps of:
   a) creating at least one transgenic Brassica plant having a seed-specific reduction in microsomal delta-12 fatty acid desaturase gene expression and a seed-specific reduction in microsomal delta-15 fatty acid desaturase gene expression, wherein said transgenic plant contains at least one recombinant nucleic acid construct, said at least one construct comprising a regulatory sequence fragment operably linked to a wild-type microsomal delta-12 fatty acid desaturase coding sequence fragment and a regulatory sequence fragment operably linked to a wild-type microsomal delta-15 fatty acid desaturase coding sequence fragment;
   b) crushing seeds produced from said plant; and
   c) extracting said oil from said seeds, said oil having an oleic acid content of about 80% or greater, an α-linolenic acid content of 2.5% or less and an erucic acid content of less than about 2%, said oleic acid content and erucic acid content determined after hydrolysis of said oil.

20. The method of claim 19, wherein said seed-specific reduction in delta-12 desaturase expression is created by cosuppression.

21. The method of claim 19, wherein said seed-specific reduction in delta-12 desaturase expression is created by antisense suppression.

22. The method of claim 19, wherein said seed-specific reduction in delta-15 desaturase expression is created by cosuppression.

23. The method of claim 19, wherein said seed-specific reduction in delta-15 desaturase expression is created by antisense suppression.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1155 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM: Brassica napus ( i x ) FEATURE:
        ( D ) OTHER INFORMATION: Wild type F form.

( x i ) SEQUENCE DESCRIPTION: SEQ ID NO:1:

```
ATG  GGT  GCA  GGT  GGA  AGA  ATG  CAA  GTG  TCT  CCT  CCC  TCC  AAG  AAG  TCT        48
Met  Gly  Ala  Gly  Gly  Arg  Met  Gln  Val  Ser  Pro  Pro  Ser  Lys  Lys  Ser
  1                       5                        10                       15

GAA  ACC  GAC  ACC  ATC  AAG  CGC  GTA  CCC  TGC  GAG  ACA  CCG  CCC  TTC  ACT        96
Glu  Thr  Asp  Thr  Ile  Lys  Arg  Val  Pro  Cys  Glu  Thr  Pro  Pro  Phe  Thr
                     20                       25                       30

GTC  GGA  GAA  CTC  AAG  AAA  GCA  ATC  CCA  CCG  CAC  TGT  TTC  AAA  CGC  TCG       144
Val  Gly  Glu  Leu  Lys  Lys  Ala  Ile  Pro  Pro  His  Cys  Phe  Lys  Arg  Ser
           35                        40                       45

ATC  CCT  CGC  TCT  TTC  TCC  TAC  CTC  ATC  TGG  GAC  ATC  ATC  ATA  GCC  TCC       192
Ile  Pro  Arg  Ser  Phe  Ser  Tyr  Leu  Ile  Trp  Asp  Ile  Ile  Ile  Ala  Ser
      50                       55                       60

TGC  TTC  TAC  TAC  GTC  GCC  ACC  ACT  TAC  TTC  CCT  CTC  CTC  CCT  CAC  CCT       240
Cys  Phe  Tyr  Tyr  Val  Ala  Thr  Thr  Tyr  Phe  Pro  Leu  Leu  Pro  His  Pro
 65                       70                       75                       80

CTC  TCC  TAC  TTC  GCC  TGG  CCT  CTC  TAC  TGG  GCC  TGC  CAA  GGG  TGC  GTC       288
Leu  Ser  Tyr  Phe  Ala  Trp  Pro  Leu  Tyr  Trp  Ala  Cys  Gln  Gly  Cys  Val
                     85                       90                       95

CTA  ACC  GGC  GTC  TGG  GTC  ATA  GCC  CAC  GAA  TGC  GGC  CAC  CAC  GCC  TTC       336
Leu  Thr  Gly  Val  Trp  Val  Ile  Ala  His  Glu  Cys  Gly  His  His  Ala  Phe
                    100                      105                      110

AGC  GAC  TAC  CAG  TGG  CTT  GAC  GAC  ACC  GTC  GGT  CTC  ATC  TTC  CAC  TCC       384
Ser  Asp  Tyr  Gln  Trp  Leu  Asp  Asp  Thr  Val  Gly  Leu  Ile  Phe  His  Ser
               115                      120                      125

TTC  CTC  CTC  GTC  CCT  TAC  TTC  TCC  TGG  AAG  TAC  AGT  CAT  CGA  CGC  CAC       432
Phe  Leu  Leu  Val  Pro  Tyr  Phe  Ser  Trp  Lys  Tyr  Ser  His  Arg  Arg  His
     130                      135                      140

CAT  TCC  AAC  ACT  GGC  TCC  CTC  GAG  AGA  GAC  GAA  GTG  TTT  GTC  CCC  AAG       480
His  Ser  Asn  Thr  Gly  Ser  Leu  Glu  Arg  Asp  Glu  Val  Phe  Val  Pro  Lys
145                      150                      155                      160
```

| | | | | | | | | | | | | | | | | |
|---|---|---|---|---|---|---|---|---|---|---|---|---|---|---|---|---|
| AAG | AAG | TCA | GAC | ATC | AAG | TGG | TAC | GGC | AAG | TAC | CTC | AAC | AAC | CCT | TTG | 528 |
| Lys | Lys | Ser | Asp | Ile | Lys | Trp | Tyr | Gly | Lys | Tyr | Leu | Asn | Asn | Pro | Leu | |
| | | | | 165 | | | | 170 | | | | | | 175 | | |
| GGA | CGC | ACC | GTG | ATG | TTA | ACG | GTT | CAG | TTC | ACT | CTC | GGC | TGG | CCG | TTG | 576 |
| Gly | Arg | Thr | Val | Met | Leu | Thr | Val | Gln | Phe | Thr | Leu | Gly | Trp | Pro | Leu | |
| | | | 180 | | | | | 185 | | | | | 190 | | | |
| TAC | TTA | GCC | TTC | AAC | GTC | TCG | GGA | AGA | CCT | TAC | GAC | GGC | GGC | TTC | GCT | 624 |
| Tyr | Leu | Ala | Phe | Asn | Val | Ser | Gly | Arg | Pro | Tyr | Asp | Gly | Gly | Phe | Ala | |
| | | 195 | | | | | 200 | | | | | 205 | | | | |
| TGC | CAT | TTC | CAC | CCC | AAC | GCT | CCC | ATC | TAC | AAC | GAC | CGC | GAG | CGT | CTC | 672 |
| Cys | His | Phe | His | Pro | Asn | Ala | Pro | Ile | Tyr | Asn | Asp | Arg | Glu | Arg | Leu | |
| | 210 | | | | | 215 | | | | | 220 | | | | | |
| CAG | ATA | TAC | ATC | TCC | GAC | GCT | GGC | ATC | CTC | GCC | GTC | TGC | TAC | GGT | CTC | 720 |
| Gln | Ile | Tyr | Ile | Ser | Asp | Ala | Gly | Ile | Leu | Ala | Val | Cys | Tyr | Gly | Leu | |
| 225 | | | | | 230 | | | | 235 | | | | | 240 | | |
| TTC | CGT | TAC | GCC | GCC | GCG | CAG | GGA | GTG | GCC | TCG | ATG | GTC | TGC | TTC | TAC | 768 |
| Phe | Arg | Tyr | Ala | Ala | Ala | Gln | Gly | Val | Ala | Ser | Met | Val | Cys | Phe | Tyr | |
| | | | | 245 | | | | | 250 | | | | | 255 | | |
| GGA | GTC | CCG | CTT | CTG | ATT | GTC | AAT | GGT | TTC | CTC | GTG | TTG | ATC | ACT | TAC | 816 |
| Gly | Val | Pro | Leu | Leu | Ile | Val | Asn | Gly | Phe | Leu | Val | Leu | Ile | Thr | Tyr | |
| | | | 260 | | | | | 265 | | | | | 270 | | | |
| TTG | CAG | CAC | ACG | CAT | CCT | TCC | CTG | CCT | CAC | TAC | GAT | TCG | TCC | GAG | TGG | 864 |
| Leu | Gln | His | Thr | His | Pro | Ser | Leu | Pro | His | Tyr | Asp | Ser | Ser | Glu | Trp | |
| | | 275 | | | | | 280 | | | | | 285 | | | | |
| GAT | TGG | TTG | AGG | GGA | GCT | TTG | GCT | ACC | GTT | GAC | AGA | GAC | TAC | GGA | ATC | 912 |
| Asp | Trp | Leu | Arg | Gly | Ala | Leu | Ala | Thr | Val | Asp | Arg | Asp | Tyr | Gly | Ile | |
| | | 290 | | | | | 295 | | | | | 300 | | | | |
| TTG | AAC | AAG | GTC | TTC | CAC | AAT | ATT | ACC | GAC | ACG | CAC | GTG | GCG | CAT | CAT | 960 |
| Leu | Asn | Lys | Val | Phe | His | Asn | Ile | Thr | Asp | Thr | His | Val | Ala | His | His | |
| 305 | | | | | 310 | | | | | 315 | | | | | 320 | |
| CTG | TTC | TCC | ACG | ATG | CCG | CAT | TAT | CAC | GCG | ATG | GAA | GCT | ACC | AAG | GCG | 1008 |
| Leu | Phe | Ser | Thr | Met | Pro | His | Tyr | His | Ala | Met | Glu | Ala | Thr | Lys | Ala | |
| | | | | 325 | | | | 330 | | | | | 335 | | | |
| ATA | AAG | CCG | ATA | CTG | GGA | GAG | TAT | TAT | CAG | TTC | GAT | GGG | ACG | CCG | GTG | 1056 |
| Ile | Lys | Pro | Ile | Leu | Gly | Glu | Tyr | Tyr | Gln | Phe | Asp | Gly | Thr | Pro | Val | |
| | | | 340 | | | | | 345 | | | | | 350 | | | |
| GTT | AAG | GCG | ATG | TGG | AGG | GAG | GCG | AAG | GAG | TGT | ATC | TAT | GTG | GAA | CCG | 1104 |
| Val | Lys | Ala | Met | Trp | Arg | Glu | Ala | Lys | Glu | Cys | Ile | Tyr | Val | Glu | Pro | |
| | | 355 | | | | | 360 | | | | | 365 | | | | |
| GAC | AGG | CAA | GGT | GAG | AAG | AAA | GGT | GTG | TTC | TGG | TAC | AAC | AAT | AAG | TTA T | 1153 |
| Asp | Arg | Gln | Gly | Glu | Lys | Lys | Gly | Val | Phe | Trp | Tyr | Asn | Asn | Lys | Leu | |
| | | 370 | | | | 375 | | | | | 380 | | | | | |
| GA | | | | | | | | | | | | | | | | 1155 |

( 2 ) INFORMATION FOR SEQ ID NO:2:

( i ) SEQUENCE CHARACTERISTICS:
        ( A ) LENGTH: 384 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Gly | Ala | Gly | Gly | Arg | Met | Gln | Val | Ser | Pro | Pro | Ser | Lys | Lys | Ser |
| 1 | | | | 5 | | | | | 10 | | | | | 15 |
| Glu | Thr | Asp | Thr | Ile | Lys | Arg | Val | Pro | Cys | Glu | Thr | Pro | Pro | Phe | Thr |
| | | | 20 | | | | | 25 | | | | | 30 | | |
| Val | Gly | Glu | Leu | Lys | Lys | Ala | Ile | Pro | Pro | His | Cys | Phe | Lys | Arg | Ser |
| | | | 35 | | | | | 40 | | | | | 45 | | |

```
Ile  Pro  Arg  Ser  Phe  Ser  Tyr  Leu  Ile  Trp  Asp  Ile  Ile  Ile  Ala  Ser
     50                  55                  60

Cys  Phe  Tyr  Tyr  Val  Ala  Thr  Thr  Tyr  Phe  Pro  Leu  Leu  Pro  His  Pro
65                       70                  75                            80

Leu  Ser  Tyr  Phe  Ala  Trp  Pro  Leu  Tyr  Trp  Ala  Cys  Gln  Gly  Cys  Val
                    85                       90                            95

Leu  Thr  Gly  Val  Trp  Val  Ile  Ala  His  Glu  Cys  Gly  His  His  Ala  Phe
               100                      105                      110

Ser  Asp  Tyr  Gln  Trp  Leu  Asp  Asp  Thr  Val  Gly  Leu  Ile  Phe  His  Ser
               115                 120                      125

Phe  Leu  Leu  Val  Pro  Tyr  Phe  Ser  Trp  Lys  Tyr  Ser  His  Arg  Arg  His
     130                      135                 140

His  Ser  Asn  Thr  Gly  Ser  Leu  Glu  Arg  Asp  Glu  Val  Phe  Val  Pro  Lys
145                      150                 155                            160

Lys  Lys  Ser  Asp  Ile  Lys  Trp  Tyr  Gly  Lys  Tyr  Leu  Asn  Asn  Pro  Leu
                    165                 170                      175

Gly  Arg  Thr  Val  Met  Leu  Thr  Val  Gln  Phe  Thr  Leu  Gly  Trp  Pro  Leu
               180                      185                      190

Tyr  Leu  Ala  Phe  Asn  Val  Ser  Gly  Arg  Pro  Tyr  Asp  Gly  Gly  Phe  Ala
          195                      200                      205

Cys  His  Phe  His  Pro  Asn  Ala  Pro  Ile  Tyr  Asn  Asp  Arg  Glu  Arg  Leu
     210                      215                      220

Gln  Ile  Tyr  Ile  Ser  Asp  Ala  Gly  Ile  Leu  Ala  Val  Cys  Tyr  Gly  Leu
225                      230                      235                       240

Phe  Arg  Tyr  Ala  Ala  Ala  Gln  Gly  Val  Ala  Ser  Met  Val  Cys  Phe  Tyr
                    245                      250                      255

Gly  Val  Pro  Leu  Leu  Ile  Val  Asn  Gly  Phe  Leu  Val  Leu  Ile  Thr  Tyr
               260                      265                      270

Leu  Gln  His  Thr  His  Pro  Ser  Leu  Pro  His  Tyr  Asp  Ser  Ser  Glu  Trp
          275                      280                      285

Asp  Trp  Leu  Arg  Gly  Ala  Leu  Ala  Thr  Val  Asp  Arg  Asp  Tyr  Gly  Ile
     290                      295                      300

Leu  Asn  Lys  Val  Phe  His  Asn  Ile  Thr  Asp  Thr  His  Val  Ala  His  His
305                      310                      315                       320

Leu  Phe  Ser  Thr  Met  Pro  His  Tyr  His  Ala  Met  Glu  Ala  Thr  Lys  Ala
                    325                      330                      335

Ile  Lys  Pro  Ile  Leu  Gly  Glu  Tyr  Tyr  Gln  Phe  Asp  Gly  Thr  Pro  Val
               340                      345                      350

Val  Lys  Ala  Met  Trp  Arg  Glu  Ala  Lys  Glu  Cys  Ile  Tyr  Val  Glu  Pro
          355                      360                      365

Asp  Arg  Gln  Gly  Glu  Lys  Lys  Gly  Val  Phe  Trp  Tyr  Asn  Asn  Lys  Leu
     370                      375                      380
```

( 2 ) INFORMATION FOR SEQ ID NO:3:

( i ) SEQUENCE CHARACTERISTICS:
        ( A ) LENGTH: 1155 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v ) ORIGINAL SOURCE:
        ( A ) ORGANISM: Brassica napus (vii) IMMEDIATE SOURCE:
  (B) CLONE: IMC129

(ix) FEATURE:
  (D) OTHER INFORMATION: G to A transversion
    mutation at nucleotide 316 of the D form.

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GGT | GCA | GGT | GGA | AGA | ATG | CAA | GTG | TCT | CCT | CCC | TCC | AAA | AAG | TCT | 48 |
| Met | Gly | Ala | Gly | Gly | Arg | Met | Gln | Val | Ser | Pro | Pro | Ser | Lys | Lys | Ser | |
| 1 | | | | 5 | | | | | 10 | | | | | 15 | | |
| GAA | ACC | GAC | AAC | ATC | AAG | CGC | GTA | CCC | TGC | GAG | ACA | CCG | CCC | TTC | ACT | 96 |
| Glu | Thr | Asp | Asn | Ile | Lys | Arg | Val | Pro | Cys | Glu | Thr | Pro | Pro | Phe | Thr | |
| | | | 20 | | | | | 25 | | | | | 30 | | | |
| GTC | GGA | GAA | CTC | AAG | AAA | GCA | ATC | CCA | CCG | CAC | TGT | TTC | AAA | CGC | TCG | 144 |
| Val | Gly | Glu | Leu | Lys | Lys | Ala | Ile | Pro | Pro | His | Cys | Phe | Lys | Arg | Ser | |
| | | 35 | | | | | 40 | | | | | 45 | | | | |
| ATC | CCT | CGC | TCT | TTC | TCC | TAC | CTC | ATC | TGG | GAC | ATC | ATC | ATA | GCC | TCC | 192 |
| Ile | Pro | Arg | Ser | Phe | Ser | Tyr | Leu | Ile | Trp | Asp | Ile | Ile | Ile | Ala | Ser | |
| | | 50 | | | | 55 | | | | | 60 | | | | | |
| TGC | TTC | TAC | TAC | GTC | GCC | ACC | ACT | TAC | TTC | CCT | CTC | CTC | CCT | CAC | CCT | 240 |
| Cys | Phe | Tyr | Tyr | Val | Ala | Thr | Thr | Tyr | Phe | Pro | Leu | Leu | Pro | His | Pro | |
| 65 | | | | | 70 | | | | | 75 | | | | | 80 | |
| CTC | TCC | TAC | TTC | GCC | TGG | CCT | CTC | TAC | TGG | GCC | TGC | CAG | GGC | TGC | GTC | 288 |
| Leu | Ser | Tyr | Phe | Ala | Trp | Pro | Leu | Tyr | Trp | Ala | Cys | Gln | Gly | Cys | Val | |
| | | | | 85 | | | | | 90 | | | | | 95 | | |
| CTA | ACC | GGC | GTC | TGG | GTC | ATA | GCC | CAC | AAG | TGC | GGC | CAC | CAC | GCC | TTC | 336 |
| Leu | Thr | Gly | Val | Trp | Val | Ile | Ala | His | Lys | Cys | Gly | His | His | Ala | Phe | |
| | | | 100 | | | | | 105 | | | | | 110 | | | |
| AGC | GAC | TAC | CAG | TGG | CTG | GAC | GAC | ACC | GTC | GGC | CTC | ATC | TTC | CAC | TCC | 384 |
| Ser | Asp | Tyr | Gln | Trp | Leu | Asp | Asp | Thr | Val | Gly | Leu | Ile | Phe | His | Ser | |
| | | 115 | | | | | 120 | | | | | 125 | | | | |
| TTC | CTC | CTC | GTC | CYT | TAC | TTC | TCC | TGG | AAG | TAC | AGT | CAT | CGA | CGC | CAC | 432 |
| Phe | Leu | Leu | Val | Xaa | Tyr | Phe | Ser | Trp | Lys | Tyr | Ser | His | Arg | Arg | His | |
| | 130 | | | | | 135 | | | | | 140 | | | | | |
| CAT | TCC | AAC | ACT | GGC | TCC | CTC | GAG | AGA | GAC | GAA | GTG | TTT | GTC | CCC | AAG | 480 |
| His | Ser | Asn | Thr | Gly | Ser | Leu | Glu | Arg | Asp | Glu | Val | Phe | Val | Pro | Lys | |
| 145 | | | | | 150 | | | | | 155 | | | | | 160 | |
| AAG | AAG | TCA | GAC | ATC | AAG | TGG | TAC | GGC | AAG | TAC | CTC | AAC | AAC | CCT | TTG | 528 |
| Lys | Lys | Ser | Asp | Ile | Lys | Trp | Tyr | Gly | Lys | Tyr | Leu | Asn | Asn | Pro | Leu | |
| | | | | 165 | | | | | 170 | | | | | 175 | | |
| GGA | CGC | ACC | GTG | ATG | TTA | ACG | GTT | CAG | TTC | ACT | CTC | GGC | TGG | CCT | TTG | 576 |
| Gly | Arg | Thr | Val | Met | Leu | Thr | Val | Gln | Phe | Thr | Leu | Gly | Trp | Pro | Leu | |
| | | | 180 | | | | | 185 | | | | | 190 | | | |
| TAC | TTR | GCC | TTC | AAC | GTC | TCG | GGG | AGA | CCT | TAC | GAC | GGC | GGC | TTC | GCT | 624 |
| Tyr | Leu | Ala | Phe | Asn | Val | Ser | Gly | Arg | Pro | Tyr | Asp | Gly | Gly | Phe | Ala | |
| | | 195 | | | | | 200 | | | | | 205 | | | | |
| TGC | CAT | TTC | CAC | CCC | AAC | GCT | CCC | ATC | TAC | AAC | GAC | CGT | GAG | CGT | CTC | 672 |
| Cys | His | Phe | His | Pro | Asn | Ala | Pro | Ile | Tyr | Asn | Asp | Arg | Glu | Arg | Leu | |
| | 210 | | | | | 215 | | | | | 220 | | | | | |
| CAG | ATA | TAC | ATC | TCC | GAC | GCT | GGC | ATC | CTC | GCC | GTC | TGC | TAC | GGT | CTC | 720 |
| Gln | Ile | Tyr | Ile | Ser | Asp | Ala | Gly | Ile | Leu | Ala | Val | Cys | Tyr | Gly | Leu | |
| 225 | | | | | 230 | | | | | 235 | | | | | 240 | |
| TAC | CGC | TAC | GCT | GCT | RTC | CAA | GGA | GTT | GCC | TCG | ATG | GTC | TGC | TTC | TAC | 768 |
| Tyr | Arg | Tyr | Ala | Ala | Xaa | Gln | Gly | Val | Ala | Ser | Met | Val | Cys | Phe | Tyr | |
| | | | | 245 | | | | | 250 | | | | | 255 | | |
| GGA | GTT | CCT | CTT | CTG | RTT | GTC | AAC | GGG | TTC | TTA | GTT | TTG | ATC | ACT | TAC | 816 |
| Gly | Val | Pro | Leu | Leu | Xaa | Val | Asn | Gly | Phe | Leu | Val | Leu | Ile | Thr | Tyr | |
| | | | 260 | | | | | 265 | | | | | 270 | | | |

| | | | | | | | | | | | | | | | |
|---|---|---|---|---|---|---|---|---|---|---|---|---|---|---|---|
| TTG | CAG | CAC | ACG | CAT | CCT | TCC | CTG | CCT | CAC | TAT | GAC | TCG | TCT | GAG | TGG | 864 |
| Leu | Gln | His | Thr | His | Pro | Ser | Leu | Pro | His | Tyr | Asp | Ser | Ser | Glu | Trp |
| | | 275 | | | | 280 | | | | | 285 | | | | |
| GAT | TGG | TTG | AGG | GGA | GCT | TTG | GCC | ACC | GTT | GAC | AGA | GAC | TAC | GGA | ATC | 912 |
| Asp | Trp | Leu | Arg | Gly | Ala | Leu | Ala | Thr | Val | Asp | Arg | Asp | Tyr | Gly | Ile |
| 290 | | | | | 295 | | | | | | 300 | | | | |
| TTG | AAC | AAG | GTC | TTC | CAC | AAT | ATC | ACG | GAC | ACG | CAC | GTG | GCG | CAT | CAC | 960 |
| Leu | Asn | Lys | Val | Phe | His | Asn | Ile | Thr | Asp | Thr | His | Val | Ala | His | His |
| 305 | | | | | 310 | | | | | 315 | | | | | 320 |
| CTG | TTC | TCG | ACC | ATG | CCG | CAT | TAT | CAT | GCG | ATG | GAA | GCT | ACG | AAG | GCG | 1008 |
| Leu | Phe | Ser | Thr | Met | Pro | His | Tyr | His | Ala | Met | Glu | Ala | Thr | Lys | Ala |
| | | | | 325 | | | | | 330 | | | | | 335 | |
| ATA | AAG | CCG | ATA | CTG | GGA | GAG | TAT | TAY | CAG | TTC | GAT | GGG | ACG | CCG | GTG | 1056 |
| Ile | Lys | Pro | Ile | Leu | Gly | Glu | Tyr | Tyr | Gln | Phe | Asp | Gly | Thr | Pro | Val |
| | | | 340 | | | | | 345 | | | | | 350 | | |
| GTT | AAG | GCG | ATG | TGG | AGG | GAG | GCG | AAG | GAG | TGT | ATC | TAT | GTG | GAA | CCG | 1104 |
| Val | Lys | Ala | Met | Trp | Arg | Glu | Ala | Lys | Glu | Cys | Ile | Tyr | Val | Glu | Pro |
| | | 355 | | | | | 360 | | | | | 365 | | | |
| GAC | AGG | CAA | GGT | GAG | AAG | AAA | GGT | GTG | TTC | TGG | TAC | AAC | AAT | AAG | TTA | T 1153 |
| Asp | Arg | Gln | Gly | Glu | Lys | Lys | Gly | Val | Phe | Trp | Tyr | Asn | Asn | Lys | Leu |
| | 370 | | | | 375 | | | | | 380 | | | | | |
| GA | | | | | | | | | | | | | | | | 1155 |

(2) INFORMATION FOR SEQ ID NO:4:

(i) SEQUENCE CHARACTERISTICS:
(A) LENGTH: 384 amino acids
(B) TYPE: amino acid
(D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met | Gly | Ala | Gly | Gly | Arg | Met | Gln | Val | Ser | Pro | Pro | Ser | Lys | Lys | Ser |
| 1 | | | | 5 | | | | | 10 | | | | | 15 | |
| Glu | Thr | Asp | Asn | Ile | Lys | Arg | Val | Pro | Cys | Glu | Thr | Pro | Pro | Phe | Thr |
| | | | 20 | | | | | 25 | | | | | 30 | | |
| Val | Gly | Glu | Leu | Lys | Lys | Ala | Ile | Pro | Pro | His | Cys | Phe | Lys | Arg | Ser |
| | | 35 | | | | | 40 | | | | | 45 | | | |
| Ile | Pro | Arg | Ser | Phe | Ser | Tyr | Leu | Ile | Trp | Asp | Ile | Ile | Ile | Ala | Ser |
| | 50 | | | | | 55 | | | | | 60 | | | | |
| Cys | Phe | Tyr | Tyr | Val | Ala | Thr | Thr | Tyr | Phe | Pro | Leu | Leu | Pro | His | Pro |
| 65 | | | | | 70 | | | | | 75 | | | | | 80 |
| Leu | Ser | Tyr | Phe | Ala | Trp | Pro | Leu | Tyr | Trp | Ala | Cys | Gln | Gly | Cys | Val |
| | | | | 85 | | | | | 90 | | | | | 95 | |
| Leu | Thr | Gly | Val | Trp | Val | Ile | Ala | His | Lys | Cys | Gly | His | His | Ala | Phe |
| | | | 100 | | | | | 105 | | | | | 110 | | |
| Ser | Asp | Tyr | Gln | Trp | Leu | Asp | Asp | Thr | Val | Gly | Leu | Ile | Phe | His | Ser |
| | | | 115 | | | | 120 | | | | | 125 | | | |
| Phe | Leu | Leu | Val | Xaa | Tyr | Phe | Ser | Trp | Lys | Tyr | Ser | His | Arg | Arg | His |
| | 130 | | | | | 135 | | | | | 140 | | | | |
| His | Ser | Asn | Thr | Gly | Ser | Leu | Glu | Arg | Asp | Glu | Val | Phe | Val | Pro | Lys |
| 145 | | | | | 150 | | | | | 155 | | | | | 160 |
| Lys | Lys | Ser | Asp | Ile | Lys | Trp | Tyr | Gly | Lys | Tyr | Leu | Asn | Asn | Pro | Leu |
| | | | | 165 | | | | | 170 | | | | | 175 | |
| Gly | Arg | Thr | Val | Met | Leu | Thr | Val | Gln | Phe | Thr | Leu | Gly | Trp | Pro | Leu |
| | | | 180 | | | | | 185 | | | | | 190 | | |
| Tyr | Leu | Ala | Phe | Asn | Val | Ser | Gly | Arg | Pro | Tyr | Asp | Gly | Phe | Ala |
| | | 195 | | | | | 200 | | | | | 205 | | | |

```
Cys  His  Phe  His  Pro  Asn  Ala  Pro  Ile  Tyr  Asn  Asp  Arg  Glu  Arg  Leu
     210                 215                      220

Gln  Ile  Tyr  Ile  Ser  Asp  Ala  Gly  Ile  Leu  Ala  Val  Cys  Tyr  Gly  Leu
225                      230                 235                          240

Tyr  Arg  Tyr  Ala  Ala  Xaa  Gln  Gly  Val  Ala  Ser  Met  Val  Cys  Phe  Tyr
                    245                      250                     255

Gly  Val  Pro  Leu  Leu  Xaa  Val  Asn  Gly  Phe  Leu  Val  Leu  Ile  Thr  Tyr
               260                      265                          270

Leu  Gln  His  Thr  His  Pro  Ser  Leu  Pro  His  Tyr  Asp  Ser  Ser  Glu  Trp
          275                      280                      285

Asp  Trp  Leu  Arg  Gly  Ala  Leu  Ala  Thr  Val  Asp  Arg  Asp  Tyr  Gly  Ile
     290                      295                      300

Leu  Asn  Lys  Val  Phe  His  Asn  Ile  Thr  Asp  Thr  His  Val  Ala  His  His
305                      310                      315                     320

Leu  Phe  Ser  Thr  Met  Pro  His  Tyr  His  Ala  Met  Glu  Ala  Thr  Lys  Ala
                    325                      330                     335

Ile  Lys  Pro  Ile  Leu  Gly  Glu  Tyr  Tyr  Gln  Phe  Asp  Gly  Thr  Pro  Val
               340                      345                     350

Val  Lys  Ala  Met  Trp  Arg  Glu  Ala  Lys  Glu  Cys  Ile  Tyr  Val  Glu  Pro
          355                      360                      365

Asp  Arg  Gln  Gly  Glu  Lys  Lys  Gly  Val  Phe  Trp  Tyr  Asn  Asn  Lys  Leu
     370                 375                      380
```

(2) INFORMATION FOR SEQ ID NO:5:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (v) ORIGINAL SOURCE:
        (A) ORGANISM: Brassica napus (ix) FEATURE:
        (D) OTHER INFORMATION: Wild type D form.

(xi) SEQUENCE DESCRIPTION: SEQ ID NO:5:

```
ATG  GGT  GCA  GGT  GGA  AGA  ATG  CAA  GTG  TCT  CCT  CCC  TCC  AAA  AAG  TCT    48
Met  Gly  Ala  Gly  Gly  Arg  Met  Gln  Val  Ser  Pro  Pro  Ser  Lys  Lys  Ser
 1                   5                        10                      15

GAA  ACC  GAC  AAC  ATC  AAG  CGC  GTA  CCC  TGC  GAG  ACA  CCG  CCC  TTC  ACT    96
Glu  Thr  Asp  Asn  Ile  Lys  Arg  Val  Pro  Cys  Glu  Thr  Pro  Pro  Phe  Thr
                20                        25                      30

GTC  GGA  GAA  CTC  AAG  AAA  GCA  ATC  CCA  CCG  CAC  TGT  TTC  AAA  CGC  TCG   144
Val  Gly  Glu  Leu  Lys  Lys  Ala  Ile  Pro  Pro  His  Cys  Phe  Lys  Arg  Ser
           35                        40                      45

ATC  CCT  CGC  TCT  TTC  TCC  TAC  CTC  ATC  TGG  GAC  ATC  ATC  ATA  GCC  TCC   192
Ile  Pro  Arg  Ser  Phe  Ser  Tyr  Leu  Ile  Trp  Asp  Ile  Ile  Ile  Ala  Ser
      50                        55                      60

TGC  TTC  TAC  TAC  GTC  GCC  ACC  ACT  TAC  TTC  CCT  CTC  CTC  CCT  CAC  CCT   240
Cys  Phe  Tyr  Tyr  Val  Ala  Thr  Thr  Tyr  Phe  Pro  Leu  Leu  Pro  His  Pro
 65                       70                      75                      80

CTC  TCC  TAC  TTC  GCC  TGG  CCT  CTC  TAC  TGG  GCC  TGC  CAG  GGC  TGC  GTC   288
Leu  Ser  Tyr  Phe  Ala  Trp  Pro  Leu  Tyr  Trp  Ala  Cys  Gln  Gly  Cys  Val
                     85                       90                       95
```

| | | | | | | | | | | | | | | | |
|---|---|---|---|---|---|---|---|---|---|---|---|---|---|---|---|
| CTA | ACC | GGC | GTC | TGG | GTC | ATA | GCC | CAC | GAG | TGC | GGC | CAC | CAC | GCC | TTC |
| Leu | Thr | Gly | Val | Trp | Val | Ile | Ala | His | Glu | Cys | Gly | His | His | Ala | Phe |
| | | 100 | | | | | | 105 | | | | | 110 | | | 336

| AGC | GAC | TAC | CAG | TGG | CTG | GAC | GAC | ACC | GTC | GGC | CTC | ATC | TTC | CAC | TCC |
| Ser | Asp | Tyr | Gln | Trp | Leu | Asp | Asp | Thr | Val | Gly | Leu | Ile | Phe | His | Ser |
|     |     | 115 |     |     |     |     | 120 |     |     |     |     | 125 |     |     |     | 384

| TTC | CTC | CTC | GTC | CYT | TAC | TTC | TCC | TGG | AAG | TAC | AGT | CAT | CGA | CGC | CAC |
| Phe | Leu | Leu | Val | Xaa | Tyr | Phe | Ser | Trp | Lys | Tyr | Ser | His | Arg | Arg | His |
|     | 130 |     |     |     |     |     | 135 |     |     |     |     | 140 |     |     |     | 432

| CAT | TCC | AAC | ACT | GGC | TCC | CTC | GAG | AGA | GAC | GAA | GTG | TTT | GTC | CCC | AAG |
| His | Ser | Asn | Thr | Gly | Ser | Leu | Glu | Arg | Asp | Glu | Val | Phe | Val | Pro | Lys |
| 145 |     |     |     |     | 150 |     |     |     |     | 155 |     |     |     |     | 160 | 480

| AAG | AAG | TCA | GAC | ATC | AAG | TGG | TAC | GGC | AAG | TAC | CTC | AAC | AAC | CCT | TTG |
| Lys | Lys | Ser | Asp | Ile | Lys | Trp | Tyr | Gly | Lys | Tyr | Leu | Asn | Asn | Pro | Leu |
|     |     |     |     | 165 |     |     |     |     | 170 |     |     |     |     | 175 |     | 528

| GGA | CGC | ACC | GTG | ATG | TTA | ACG | GTT | CAG | TTC | ACT | CTC | GGC | TGG | CCT | TTG |
| Gly | Arg | Thr | Val | Met | Leu | Thr | Val | Gln | Phe | Thr | Leu | Gly | Trp | Pro | Leu |
|     |     |     | 180 |     |     |     |     | 185 |     |     |     |     | 190 |     |     | 576

| TAC | TTR | GCC | TTC | AAC | GTC | TCG | GGG | AGA | CCT | TAC | GAC | GGC | GGC | TTC | GCT |
| Tyr | Leu | Ala | Phe | Asn | Val | Ser | Gly | Arg | Pro | Tyr | Asp | Gly | Gly | Phe | Ala |
|     |     | 195 |     |     |     |     | 200 |     |     |     |     | 205 |     |     |     | 624

| TGC | CAT | TTC | CAC | CCC | AAC | GCT | CCC | ATC | TAC | AAC | GAC | CGT | GAG | CGT | CTC |
| Cys | His | Phe | His | Pro | Asn | Ala | Pro | Ile | Tyr | Asn | Asp | Arg | Glu | Arg | Leu |
|     | 210 |     |     |     |     | 215 |     |     |     |     | 220 |     |     |     |     | 672

| CAG | ATA | TAC | ATC | TCC | GAC | GCT | GGC | ATC | CTC | GCC | GTC | TGC | TAC | GGT | CTC |
| Gln | Ile | Tyr | Ile | Ser | Asp | Ala | Gly | Ile | Leu | Ala | Val | Cys | Tyr | Gly | Leu |
| 225 |     |     |     |     | 230 |     |     |     |     | 235 |     |     |     |     | 240 | 720

| TAC | CGC | TAC | GCT | GCT | RTC | CAA | GGA | GTT | GCC | TCG | ATG | GTC | TGC | TTC | TAC |
| Tyr | Arg | Tyr | Ala | Ala | Xaa | Gln | Gly | Val | Ala | Ser | Met | Val | Cys | Phe | Tyr |
|     |     |     |     | 245 |     |     |     |     | 250 |     |     |     |     | 255 |     | 768

| GGA | GTT | CCT | CTT | CTG | RTT | GTC | AAC | GGG | TTC | TTA | GTT | TTG | ATC | ACT | TAC |
| Gly | Val | Pro | Leu | Leu | Xaa | Val | Asn | Gly | Phe | Leu | Val | Leu | Ile | Thr | Tyr |
|     |     |     | 260 |     |     |     |     | 265 |     |     |     |     | 270 |     |     | 816

| TTG | CAG | CAC | ACG | CAT | CCT | TCC | CTG | CCT | CAC | TAT | GAC | TCG | TCT | GAG | TGG |
| Leu | Gln | His | Thr | His | Pro | Ser | Leu | Pro | His | Tyr | Asp | Ser | Ser | Glu | Trp |
|     |     | 275 |     |     |     |     | 280 |     |     |     |     | 285 |     |     |     | 864

| GAT | TGG | TTG | AGG | GGA | GCT | TTG | GCC | ACC | GTT | GAC | AGA | GAC | TAC | GGA | ATC |
| Asp | Trp | Leu | Arg | Gly | Ala | Leu | Ala | Thr | Val | Asp | Arg | Asp | Tyr | Gly | Ile |
|     |     | 290 |     |     |     |     | 295 |     |     |     |     | 300 |     |     |     | 912

|     | TTG | AAC | AAG | GTC | TTC | CAC | AAT | ATC | ACG | GAC | ACG | CAC | GTG | GCG | CAT | CAC |
|     | Leu | Asn | Lys | Val | Phe | His | Asn | Ile | Thr | Asp | Thr | His | Val | Ala | His | His |
| 305 |     |     |     |     |     | 310 |     |     |     |     | 315 |     |     |     |     | 320 | 960

| CTG | TTC | TCG | ACC | ATG | CCG | CAT | TAT | CAT | GCG | ATG | GAA | GCT | ACG | AAG | GCG |
| Leu | Phe | Ser | Thr | Met | Pro | His | Tyr | His | Ala | Met | Glu | Ala | Thr | Lys | Ala |
|     |     |     |     | 325 |     |     |     |     | 330 |     |     |     |     | 335 |     | 1008

| ATA | AAG | CCG | ATA | CTG | GGA | GAG | TAT | TAY | CAG | TTC | GAT | GGG | ACG | CCG | GTG |
| Ile | Lys | Pro | Ile | Leu | Gly | Glu | Tyr | Tyr | Gln | Phe | Asp | Gly | Thr | Pro | Val |
|     |     |     | 340 |     |     |     |     | 345 |     |     |     |     | 350 |     |     | 1056

| GTT | AAG | GCG | ATG | TGG | AGG | GAG | GCG | AAG | GAG | TGT | ATC | TAT | GTG | GAA | CCG |
| Val | Lys | Ala | Met | Trp | Arg | Glu | Ala | Lys | Glu | Cys | Ile | Tyr | Val | Glu | Pro |
|     |     | 355 |     |     |     |     | 360 |     |     |     |     | 365 |     |     |     | 1104

| GAC | AGG | CAA | GGT | GAG | AAG | AAA | GGT | GTG | TTC | TGG | TAC | AAC | AAT | AAG | TTA | T |
| Asp | Arg | Gln | Gly | Glu | Lys | Lys | Gly | Val | Phe | Trp | Tyr | Asn | Asn | Lys | Leu |
|     |     | 370 |     |     |     | 375 |     |     |     |     | 380 |     |     |     |     | 1153

GA                                                                                                                                      1155

( 2 ) INFORMATION FOR SEQ ID NO:6:

( i ) SEQUENCE CHARACTERISTICS:
        ( A ) LENGTH: 384 amino acids (B) TYPE: amino acid
(D) TOPOLOGY: linear (ii) MOLECULE TYPE: protein (xi) SEQUENCE DESCRIPTION: SEQ ID NO:6:

```
Met Gly Ala Gly Gly Arg Met Gln Val Ser Pro Pro Ser Lys Lys Ser
 1               5                  10                  15

Glu Thr Asp Asn Ile Lys Arg Val Pro Cys Glu Thr Pro Pro Phe Thr
             20                  25                  30

Val Gly Glu Leu Lys Lys Ala Ile Pro Pro His Cys Phe Lys Arg Ser
         35                  40                  45

Ile Pro Arg Ser Phe Ser Tyr Leu Ile Trp Asp Ile Ile Ala Ser
     50                  55                  60

Cys Phe Tyr Tyr Val Ala Thr Thr Tyr Phe Pro Leu Leu Pro His Pro
65              70                  75                      80

Leu Ser Tyr Phe Ala Trp Pro Leu Tyr Trp Ala Cys Gln Gly Cys Val
                 85                  90                  95

Leu Thr Gly Val Trp Val Ile Ala His Glu Cys Gly His His Ala Phe
             100                 105                 110

Ser Asp Tyr Gln Trp Leu Asp Asp Thr Val Gly Leu Ile Phe His Ser
             115                 120                 125

Phe Leu Leu Val Xaa Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                 165                 170                 175

Gly Arg Thr Val Met Leu Thr Val Gln Phe Thr Leu Gly Trp Pro Leu
             180                 185                 190

Tyr Leu Ala Phe Asn Val Ser Gly Arg Pro Tyr Asp Gly Gly Phe Ala
         195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Xaa Gln Gly Val Ala Ser Met Val Cys Phe Tyr
                 245                 250                 255

Gly Val Pro Leu Leu Xaa Val Asn Gly Phe Leu Val Leu Ile Thr Tyr
             260                 265                 270

Leu Gln His Thr His Pro Ser Leu Pro His Tyr Asp Ser Ser Glu Trp
         275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                 325                 330                 335

Ile Lys Pro Ile Leu Gly Glu Tyr Tyr Gln Phe Asp Gly Thr Pro Val
             340                 345                 350

Val Lys Ala Met Trp Arg Glu Ala Lys Glu Cys Ile Tyr Val Glu Pro
         355                 360                 365

Asp Arg Gln Gly Glu Lys Lys Gly Val Phe Trp Tyr Asn Asn Lys Leu
370                 375                 380
```